(12) United States Patent
Doctors et al.

(10) Patent No.: US 8,656,926 B2
(45) Date of Patent: *Feb. 25, 2014

(54) INTRA-ORAL DEVICE AND METHOD OF RELIEVING HEAD, NECK, FACIAL, JOINT AND TOOTH PAIN

(76) Inventors: Marc Doctors, Washington, DC (US); Randy Widen, Lusby, MD (US)

( * ) Notice: Subject to any disclaimer, the term of this patent is extended or adjusted under 35 U.S.C. 154(b) by 2 days.

This patent is subject to a terminal disclaimer.

(21) Appl. No.: 13/329,558

(22) Filed: Dec. 19, 2011

(65) Prior Publication Data

US 2012/0118298 A1    May 17, 2012

Related U.S. Application Data (63) Continuation-in-part of application No. 12/379,194, filed on Feb. 13, 2009, now Pat. No. 8,082,923.

(60) Provisional application No. 61/064,048, filed on Feb. 13, 2008.

(51) Int. Cl.
*A61C 5/14* (2006.01)

(52) U.S. Cl.
USPC .............. 128/862; 128/859; 128/861; 433/6

(58) Field of Classification Search
USPC ................ 128/848, 859, 861, 862; 433/6
See application file for complete search history.

(56) References Cited

U.S. PATENT DOCUMENTS

| | | | |
|---|---|---|---|
| 6,318,370 B1 | 11/2001 | Sempere et al. | |
| 6,516,805 B1 * | 2/2003 | Thornton | 128/848 |
| 6,666,212 B2 * | 12/2003 | Boyd, Sr. | 128/859 |
| 7,234,467 B2 * | 6/2007 | Ball | 128/848 |
| 2003/0121523 A1 | 7/2003 | Boyd | |
| 2007/0023055 A1 * | 2/2007 | Roth | 128/861 |
| 2008/0295850 A1 * | 12/2008 | Lesniak | 128/862 |

OTHER PUBLICATIONS

International Searching Authority (ISA/US), International Search Report mailed Feb. 17, 2011, International Application No. PCT/US2010/003171.

* cited by examiner

*Primary Examiner* — Patricia Bianco
*Assistant Examiner* — Keri J Nelson
(74) *Attorney, Agent, or Firm* — Hinshaw & Culbertson LLP (57) ABSTRACT

A device and method for relieving head, neck, facial, joint and tooth pain. An intra-oral device, worn over the upper or lower incisors, allows at least one opposite tooth to contact the rear wall of the device, only within the user's freeway space, and prevents upper and lower posterior teeth from contacting. The device facilitates deprogramming and releasing of the upper and lower jaw muscles. The device includes an extruded or molded shell made of a hard polycarbonate or similar hard plastic material. The internal surface of the shell may be secured in place for the user or lined with a low molding temperature thermoplastic resin, allowing the user to mold the internal aspect of the device onto and over the teeth to produce a fitted device. This relieves the stresses, strains, pains and damage that can be caused by parafunctioning of the dental neural-muscular system.

31 Claims, 4 Drawing Sheets

INTRA-ORAL DEVICE AND METHOD OF RELIEVING HEAD, NECK, FACIAL, JOINT AND TOOTH PAIN

CROSS REFERENCE TO RELATED APPLICATION

This application is a continuation-in-part of U.S. patent application Ser. No. 12/379,194, filed Feb. 13, 2009, which claims the benefit of U.S. Provisional Application No. 61/064,048, filed Feb. 13, 2008, the disclosures of which are hereby incorporated in their entireties.

FIELD OF THE INVENTION

The present invention relates generally to intra-oral devices and, in particular, a mass produced, intra-oral separator device intended to be worn by the user, for the elimination or relief of grinding, clenching, bruxing, and related parafunctional habits, as well as head, neck and jaw related pain. Grinding, clenching and bruxing and related parafunctional habits can produce structural damage to, and disease of, the teeth, gums and supporting structures including the temporomandibular joint.

BACKGROUND OF THE INVENTION

There is an enduring need for an inexpensive and effective device and method for the relief of head, neck, facial, joint and tooth pain caused by the parafunctional movement of the jaws and teeth. The design and function of the present invention are different than the prior art in form, function, cost and retail availability.

A variety of stressors affect the neuromuscular system of the head and neck. Among them are abnormal dental contacts, muscle tension and spasms, psychological stress factors, genetic predispositions, physical trauma and inflammation. In the presence of stressors the jaw muscles contract irregularly or parafunctionally causing the hitting together of the teeth. This interarch dental contact triggers headaches, both radiating and migraine, muscular tension, inflammation, structural damage to ligaments and tendons, fractures and excessive wear of the teeth, arthritic changes to the temporomandibular joint and periodontal disease. The pain generated radiates to other muscles, namely muscles for chewing and posture within the head, neck and back. The cycle of pain and structural damage thus created becomes the motivation for the efforts to design a device to minimize or eliminate these symptoms.

The prior art generally employs various platforms and protuberances to separate the teeth beyond the freeway space and beyond the physiologic rest position, making them less effective in eliminating pathologic muscle engrams and less likely to disrupt the cycle of pain and structural damage. The wider the mandible is forced to open by these platforms and protuberances, the more neuromuscular feedback is created and the less likely these devices are to disrupt the existing pathologic muscle engrams. In addition, these devices often require fittings by dental professionals and are therefore inconvenient and expensive for mass usage. By contrast, one embodiment of the device of the present invention is installed by the user, and would be relatively inexpensive at the retail level. The device of the present invention functions within the freeway space to effectively deprogram the neuromuscular system of the head and neck by preventing contact of the upper and lower posterior teeth.

The prior art focused on the use of medications for pain relief or the fabrication of devices whose goal was to separate the teeth and reposition the jaws. Typical of these devices are U.S. Pat. No. 4,671,766 to Norton; U.S. Pat. No. 4,519,386 to Sullivan; U.S. Pat. No. 5,277,203 to Hays; U.S. Pat. No. 6,581,603 to Schames; and U.S. Pats. Nos. 5,085,584; 5,513,656; 5,795,150; and 6,666,212 to Boyd.

These treatments are often extremely expensive and/or ineffective. A more effective device and treatment are needed, as well as a device that is readily and easily obtained at a reasonable cost and is simple to install and use.

The present invention takes into account the need to eliminate the forced positioning of a person's mandible to or beyond the physiologic rest position. The freeway space, or interocclusal space, is defined as the distance between the physiologic rest position and the first point of contact of the upper and lower teeth when the jaws are brought together. The freeway space has been observed to usually be between 2 and 7 millimeters (mm) with an approximate average for adults of 3.5 mm. The physiologic rest position is the position assumed by the mandible when the head is in an upright position, the neuromuscular system is in equilibrium in minimum tonic contraction and the condyles are at rest. The more an intra-oral device forces the mandible to open beyond the physiologic rest position, the more active neuromuscular feedback mechanisms become. This feedback triggers pathologic engrams. An engram is a memorized pattern of muscle activity. Pathologic engrams may also be remediated or eliminated by occlusal adjustment, occlusal reconstruction, retraining or through the use of medication. Thus the cycle of pain and structural damage can be interrupted temporarily or permanently. Prior art devices and methods cause the mandible to be forced open beyond the limit of the freeway space, making them less likely to interrupt the cycle of pain and structural damage. What is needed, then, are a device and method that functions only within the freeway space, while effecting disclusion of the posterior teeth and maintaining clearance within the freeway space, thereby eliminating or significantly reducing pathologic engrams.

The prior art, directed to the reduction of headaches and temporomandibular joint (TMJ) pain, functions outside of a user's freeway space. In one of its aspects, the present invention provides a device that may be installed by a dental professional to fit a user. In another aspect, the present invention allows a user to fit the device to function only within the freeway space.

Posterior disclusion with an anterior bite device is based on the concept that the temporomandibular joint will seat itself physiologically if the proprioceptive interferences of the teeth and periodontal ligaments are removed. Thus the neuromuscular system will function freely within the freeway space. Once a user's pathologic muscle engrams have been eliminated, the temporomandibular joint becomes stable. In order to decrease the likelihood of the cycle of pain and structural damage returning, an occlusal adjustment with or without occlusal reconstruction may be necessary.

SUMMARY OF THE INVENTION

In one embodiment of the present invention, the external shell of the claimed device allows for the user to fit the device close to the incisal, lingual and labial surfaces of the upper or lower anterior teeth, also referred to as upper or lower incisors. Contact on the device by the opposite incisors, only within the freeway space, promotes more predictable release of muscle engrams than contact on a device outside the freeway space. In addition, devices according to the invention may either be fitted by dental professionals or designed for easy adaptation by a user. It is anticipated the device will be moderately priced and affordable by the great majority of those who need it.

Another embodiment of the present invention relates to an intra-oral device comprising a body having a substantially angled front wall and a substantially angled rear wall, the front wall having an inner and outer surface and the rear wall having an inner and outer surface; wherein the front and rear walls are positioned to receive the incisal edges of a user's upper or lower incisors; wherein the outer surface of the wall that faces the incisors of the opposite arch is configured within the user's freeway space to contact at least one opposite incisor at an area of contact only within the user's freeway space to prevent contact between the user's upper and lower teeth; wherein the inner surface of the front wall is configured to be placed adjacent to the labial surface, and the inner surface of the rear wall adjacent to the lingual surface, of the user's upper or lower incisors.

Still another embodiment of the present invention relates to a method for relieving head, neck, facial, joint and tooth pain, the method comprising placing a device within a user's oral cavity, the device having an angled front wall and an angled rear wall, each wall with an inner and outer surface, wherein the angles of the front wall and the rear wall form an apex, optionally with moldable thermoplastic resin disposed along the inner surfaces of the front and rear wall. The apex is configured to receive the incisal edges of a user's upper or lower incisors. The device is positioned such that the inner surface of the front wall of the device is adjacent to the labial surface, and the inner surface of the rear wall adjacent to the lingual surface, of the user's upper or lower incisors; and the device is configured to contact at least one opposite incisor to prevent contact between a user's upper and lower teeth.

Yet another embodiment of the present invention relates to a method for manufacturing an intra-oral device, the method comprising forming a hard plastic resin shell having an angled front wall and an angled rear wall, each wall with an inner and outer surface, wherein the angles of the front wall and the rear wall form an apex, optionally with moldable thermoplastic resin disposed along the inner surfaces of the front and rear wall, the apex configured to receive the incisal edges of a user's upper or lower incisors. The inner surface of the front wall of the device is configured to fit substantially flush against the labial surface, and the inner surface of the rear wall to fit substantially flush against the lingual surface, of a user's upper or lower incisors. Alternatively, the method includes molding the hard plastic shell to form a device of unitary construction secured to a user's teeth.

Still another embodiment of the present invention relates to an intra-oral device comprising a body having a substantially angled front wall and a substantially angled rear wall, the front wall having an inner and outer surface and the rear wall having an inner and outer surface. Moldable thermoplastic resin material capable of being molded by a user is optionally disposed along the inner surfaces of the front and rear walls, and the front and rear walls are positioned to receive the incisal edges of a user's upper or lower incisors; wherein the outer surface of the wall that faces the incisors of the opposite arch is configured to contact at least one opposite incisor at an area of contact only within the user's freeway space to prevent contact between the user's upper and lower teeth; wherein the inner surface of the front wall is configured to be placed adjacent to the labial surface, and the inner surface of the rear wall to be placed adjacent to the lingual surface, of the user's upper or lower incisors.

In other embodiments of the invention, intra-oral devices are provided that do not necessarily have front and rear walls meeting to form an apex, resulting in a "V"-shaped profile to straddle the labial and lingual surfaces of the teeth to which they are mounted. Rather, a device according to the invention may be removably secured in place to a user's upper or lower incisors by any suitable means, including but not limited to thermoplastic forming, spring loading, cementation, thermoplastic resin molding, pressure fit, bonding, adhering, or friction fit.

These and other objects and advantages of the invention will be apparent from the following description, the accompanying drawings and the appended claims.

DETAILED DESCRIPTION OF THE INVENTION

The present disclosure will now be described more fully with reference to the Figures in which various embodiments of the present invention are shown. The subject matter of this disclosure may, however, be embodied in many different forms and should not be construed as being limited to the embodiments set forth herein.

Before explaining the features of this embodiment of the invention in detail, it should be understood that the invention is not limited in its application to the details of construction and arrangement of components set forth in the following description or illustrations in the drawings. The invention is capable of other embodiments and variations that will occur to those skilled in the art upon reading this disclosure. Also, it is to be understood that the phraseology and terminology used herein are for the purpose of description and should not be regarded as limiting.

As illustrated in FIGS. 1-4, an interocclusal separator device 10, constructed in accordance with one embodiment of the present invention, is comprised of a hard plastic resin main body at 10 with a layer of moldable thermoplastic resin 13 disposed upon the inner surfaces of the main body at 10 which is configured to be positioned on a user's teeth. In particular, the main body at 10 is comprised of an angled front wall 11 and an angled rear wall 12. Front wall 11 approximates the angle and configuration of the labial surfaces of maxillary (also termed "upper" herein) incisors U and anterior maxillary dental arch and the rear wall 12 approximates the angle and configuration of the lingual surfaces of maxillary anterior incisors U and anterior maxillary dental arch. In one or more embodiments, the front wall 11 is configured to fit substantially flush against the labial surface of a user's upper incisors U. In one or more embodiments, rear wall 12 is configured to fit substantially flush against the lingual surface of a user's upper incisors U and to contact the user's lower incisors L only within the user's freeway space F, as illustrated for example in FIG. 2, with freeway space F being indicated by the double arrow extending from upper incisor U through area of contact 18 to the position of a lower incisor at the physiologic rest position PRP, depicted in phantom lines. As further illustrated in FIG. 2a, where lower incisor L is depicted in the physiologic rest position PRP, lower incisor L does not contact outer surface 16 or any other part of the device when the mandible is at physiologic rest, and thus, nor do any of the lower teeth. A clearance C is shown in FIG. 2a between lower incisor L and outer surface 16.

Front wall 11 and rear wall 12 meet to form an apex 15 approximating the angle of the labial and lingual surfaces of upper incisors U. Apex 15 is configured to receive the incisal edges of upper incisors U. As is apparent in FIG. 2 and FIG. 4, when the device is in place, the incisal edges of lower incisors L contact outer surface 16 within freeway space F when the user's jaw closes, preventing the lower posterior teeth from coming into contact with the upper posterior teeth. Lower incisors L are in contact with the device as the mandible nears the end of its hinge arc of closure in one embodiment. The thickness between outer surface 16 and inner surface 17 is approximately 1.00 mm. The thickness of moldable thermoplastic resin 13 is initially approximately 0.5 mm, before the device is fit, but resin 13 is reduced to a negligible thickness by spreading and forming when resin 13 is at a molding temperature and a user pushes the device 10 against the user's upper incisors U to fit the device. Thus, the total approximate distance after the device is fit between a user's upper and lower incisors L when the user's lower incisors L contact the device is approximately 1.00 mm, where the inner surface of the outer shell 16 becomes substantially flush against the lingual surface of the user's upper incisors U so that the device is disposed within the freeway space F. While an embodiment of the present invention is described above with specificity, one skilled in the art recognizes that the thickness between the outer surface and inner surface, as well as the thickness of the moldable thermoplastic resin may vary, although keeping these layers purposely thin is imperative to ensure that the device functions within the freeway space, leaving a clearance C within freeway space F, so that the lower teeth of the user do not contact the device and cause the mandible to open beyond the physiologic rest position when the device is worn in accordance with the invention.

The moldable thermoplastic resin 13 may be comprised of moldable thermoplastic acetate co-polymer resin, such as a DuPont Elvax® or other ethylene vinyl acetate copolymer resin, a polycaprolactone resin, another material with similar properties, or a mixture of materials with similar properties, fixed in place on the inner surfaces of front wall 11 and rear wall 12. Thermoplastic flow properties of the selected material or mixture of materials on tooth surfaces at a suitable molding temperature influence how well the device may be fitted to the incisors, which in turn influences how well the device will be retained in a user's mouth. Melt flow index ("MFI") is a measurement of the mass flow rate of extrusion of a resin through an orifice of defined dimensions at a specified extrusion temperature and load. In experiments performed on polycaprolactone resins of different molecular weights, using a 2.16 kg load, a 1-inch diameter round PVC die, and a resin extrusion temperature of either 80° C. or 160° C. as indicated, the resulting MFI's in decigrams/minute (dg/min) were as indicated in the below Table:

TABLE

|  | Molecular Wt. (g/mol) | MFI (dg/min)/ Extrusion Temp (° C.) | Melting point (° C.) |
| --- | --- | --- | --- |
| Polycaprolactone | 25,000 | 9/80 | 58-60 |
| Polycaprolactone | 37,000 | 40/160 | 58-60 |
| Polycaprolactone | 43,000 | 13/160 | 58-60 |
| Polycaprolactone | 50,000 | 7/160 | 58-60 |

Figure 1:
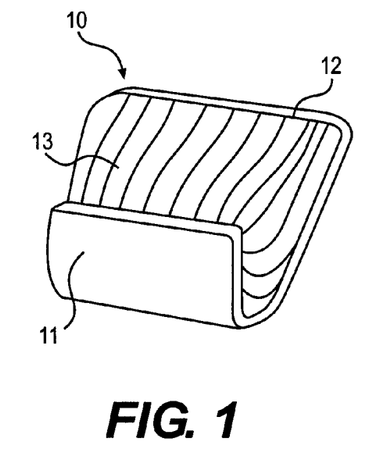
FIG. 1 shows a perspective view of an embodiment of the present invention as seen from an inferior-anterior-lateral view with moldable thermoplastic resin material installed inside a hard plastic resin shell.
Figure 2:
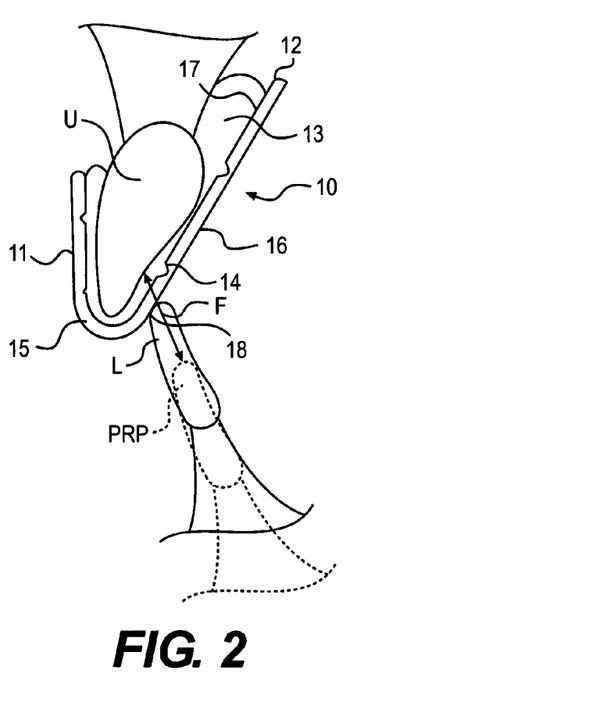
FIG. 2 shows a central section of the embodiment of the present invention of FIG. 1, with a user's upper incisors in place in the device and the user's lower incisors in contact within the user's freeway space on the outer surface of the rear wall of the device.
Figure 2A:
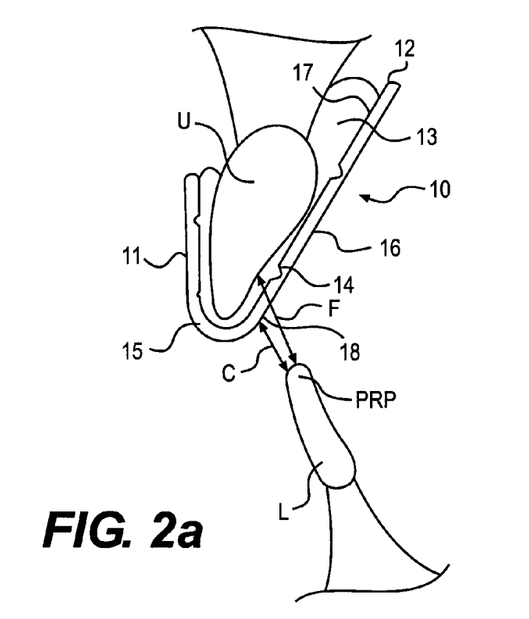
FIG. 2a shows a central section of the embodiment of the present invention of FIG. 1 with upper incisors in place in the device and the lower teeth in the physiologic rest position and not in contact with the device.

Thermoplastic resin 13 may be fixed in place on front wall 11 and rear wall 12 by detents 14, as shown in FIG. 2. The moldable thermoplastic resin may also be retained and/or adhered on the inner surfaces of walls 11 and 12 by use of adhesive, mechanical restraints, or any other similar attachment means known in the art.

In the above-described embodiment, to fit the device, the device is placed in water at a sufficiently high temperature to soften the moldable thermoplastic resin and so that the resin remains softened for a sufficient time for a user to fit and mold the device in the user's mouth. If thermoplastic resin 13 is one of the polycaprolactone materials tabulated above, it is desirable to heat the device in water at a suitable temperature to heat resin 13 to a temperature above its melting temperature of about 58-60° C. (136-140° F.), but not significantly above 82° C. (180° F.), as a user's mouth typically will not comfortably tolerate temperatures above around 180° F. Among the polycaprolactone materials, it was found that the 37,000 g/mol polycaprolactone seems to flow the best around a user's teeth, though the other materials may be suitable as well. Other suitable materials may have lower melting/softening temperatures, but they should not be significantly lower than around 120° F., to avoid the material softening and deforming from its fitted and molded shape during normal use and/or in the event that the device is stored in a hot place, such as a hot vehicle, for example. Once heated, the device is then fitted and molded by the user. To fit and mold the device, the user pushes the softened moldable thermoplastic resin onto upper incisors U until the teeth "seat" to the apex of the interior angle between front and rear walls 11 and 12 of the device. The user then closes mandibular (also termed "lower" herein) incisors L against outer surface 16 of device 10 to adapt device 10 substantially flush against the lingual surfaces of upper incisors U within device 10.

Figure 3:
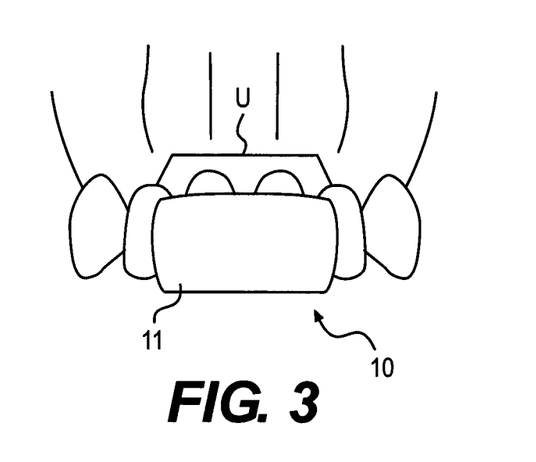
FIG. 3 shows an anterior perspective view of the embodiment of the invention of FIG. 1 in place on the user's upper incisors.

FIG. 3 shows a front view of the extent of coverage of an embodiment of the present invention in place on the upper anterior teeth.

Figure 4:
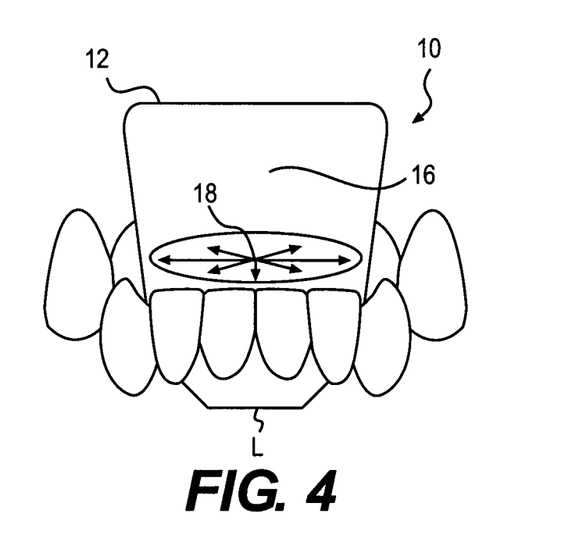
FIG. 4 shows a rear perspective view of the embodiment of the invention of FIG. 1 in place on the user's upper incisors indicating the area of contact, within the user's freeway space, of the user's lower teeth on the outer surface of the rear wall of the device.

FIG. 4 shows an area of contact 18 of the mandibular incisors L which allows mandibular incisors L to proprioceptively sense contact within the freeway space with outer surface 16 of an embodiment of the present invention, and to initiate release of parafunctional pathologic muscle engrams. More particularly, the reprogramming of muscle engrams can lead to the reduction of symptoms of parafunction from occlusal stress or psychological initiators. In one or more embodiments, by effecting the release of pathologic muscle engrams because the device functions only within the freeway space, the device of the invention may proprioceptively, as opposed to forcibly, direct the user's mandible to the physiologic rest position.

The claimed device functions in the gap between the physiologic rest position and the first contact with the device by the user's lower anterior teeth, which is illustrated in FIG. 2. The gap within the freeway space where no contact occurs between the claimed device and the lower anterior teeth creates a zone of proprioceptive awareness and permits the reflex that guides the user's mandible back to the physiologic rest position, thus effecting muscle relaxation. The claimed device creates a point of reference along the arc of closure, within the freeway space, at which the mandibular teeth proprioceptively sense the first point of contact with the device. Contact of lower incisors L with the device at that point of reference, when the user's mandible is already closed past the physiologic rest position, causes a natural relaxation response in which the jaw muscles reflexively relax and the mandible reflexively opens to the physiologic rest position, upon sensing the contact.

Figure 5:
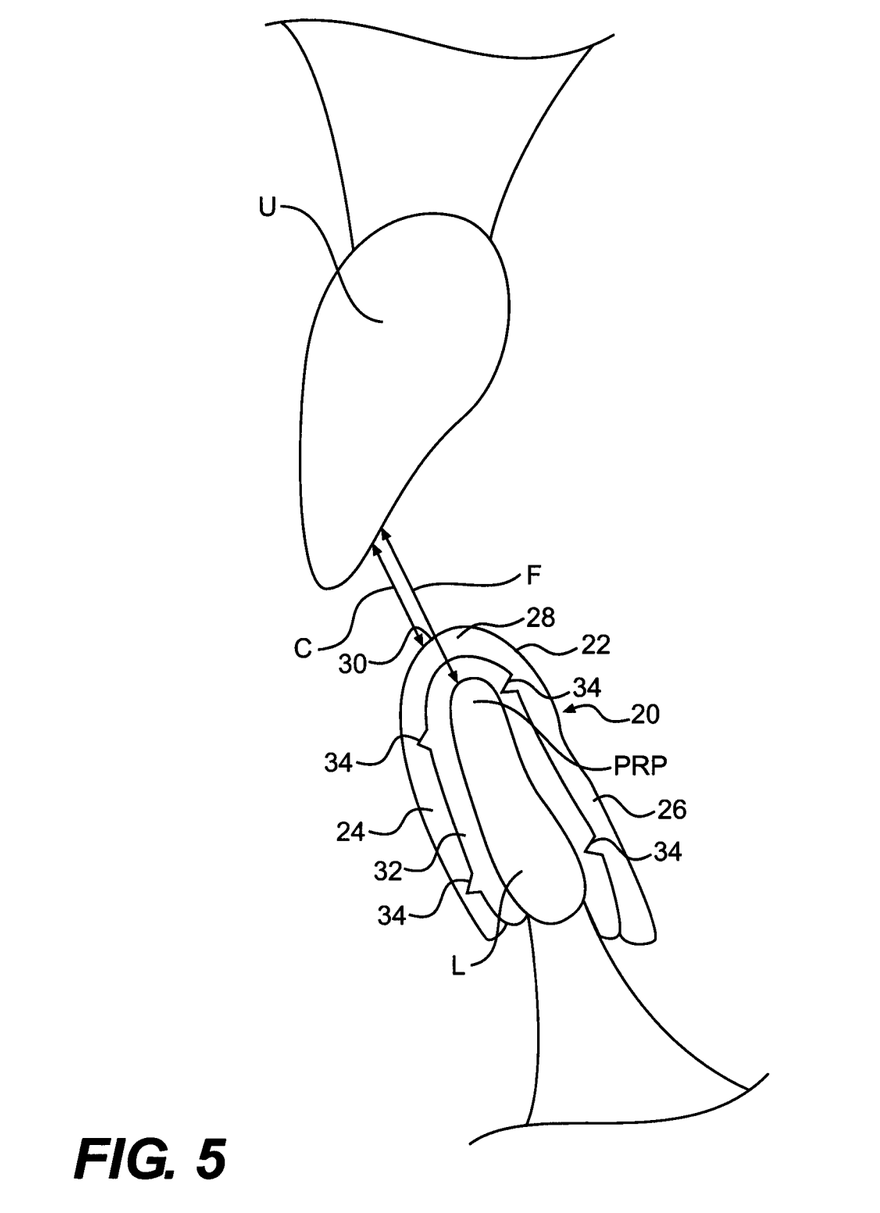
FIG. 5 shows a central section of an alternative embodiment of the present invention with lower incisors in place in the device and the mandible in the physiologic rest position, the upper teeth being not in contact with the device.

FIG. 5 is an illustration of an alternative embodiment of a lower-mounted device 20 according to the invention that is adapted to fit on a user's lower incisors L in substantially the same manner as described above for upper-mounted device 10. In particular, device 20 includes a hard plastic resin main body 22, comprised of a front wall 24 and a rear wall 26 meeting to form an apex 28 configured to receive the incisal edges of a user's lower incisors L. An inner surface of front wall 24 is designed to fit substantially flush against the labial surface, and an inner surface of rear wall 26 to fit substantially flush against the lingual surface, of lower incisors L when the device is worn by the user in accordance with the invention.

Device 20 also functions in a manner substantially similar to that of device 10. Device 20 fits wholly within the limits of the user's freeway space, i.e., device 20 is configured so that when a user's upper incisors U contact device 20, contact occurs only at an area of contact 30 that is wholly within the user's freeway space. Device 20 does not contact upper incisors U, or any of the user's other upper teeth, when the user's lower jaw is in the physiologic rest position indicated as PRP in FIG. 5. Rather, device 20 is configured to maintain a clearance C from upper incisors U, within freeway space F, when the user's jaw is at rest. As in device 10, a layer of moldable thermoplastic resin 32 may optionally be disposed over the inner surfaces of main body 22 in an embodiment, retained by detents 34 or by other suitable means.

Although devices 10 and 20 are described and illustrated with reference to FIGS. 1-5 as being formed from hard plastic resin with moldable thermoplastic resin affixed thereto alternative upper and lower mounted intra-oral devices may be formed in any suitable manner so that an area of contact of the devices is configured to be secured at a position within a user's freeway space, the area of contact only contacting the teeth of the user's opposite arch when the user's jaw closes past the physiologic rest position. In some embodiments, the entire device may be rigid, or the entire device may be flexible, in which cases the device may or may not be formed from a single material. In other embodiments, the device does not necessarily have front and rear walls meeting to form an apex, resulting in a "V"-shaped profile to straddle the labial and lingual surfaces of the teeth to which it is mounted. Rather, a device according to the invention may be removably secured in place to a user's upper or lower incisors by any suitable means, including but not limited to thermoplastic forming, spring loading, cementation, thermoplastic resin molding, pressure fit, bonding, adhering, or friction fit. While a "V"-shaped profile may be desirable to obtain a good friction fit as illustrated in FIGS. 1-5, other means of securing the device in place do not necessarily require or benefit from the device being in contact with both the lingual and labial surfaces of the teeth to which the device is mounted.

Figure 6:
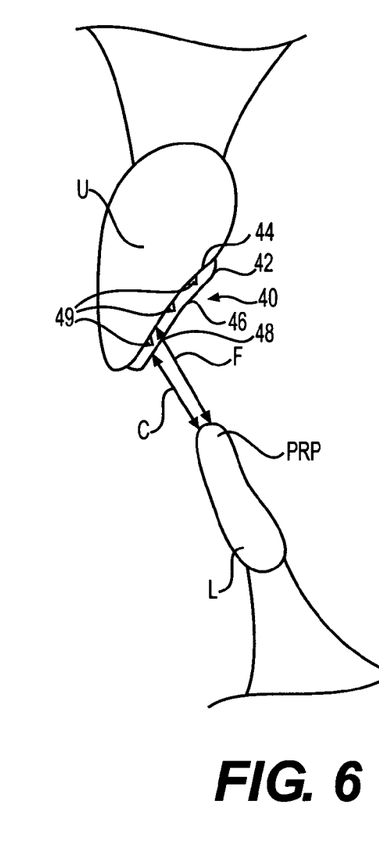
FIG. 6 shows a central section of an alternative embodiment of the present invention in which a device is mounted on a user's upper incisors by being secured in contact with the lingual surface of the user's upper incisors.
Figure 7:
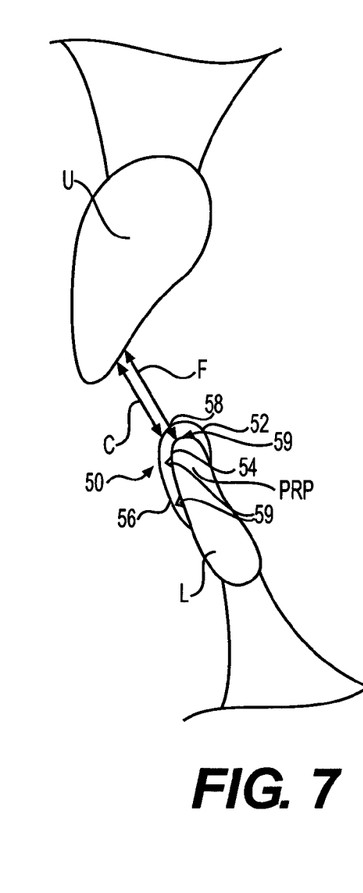
FIG. 7 shows a central section of an alternative embodiment of the present invention in which a device is mounted on a user's lower dental arch by being secured in contact with the labial surface and incisal edge of the user's lower incisors.

To illustrate certain variations that are possible within the scope of the invention, with reference to FIGS. 6 and 7, alternative devices 40 and 50 are depicted, which are secured only to the surface of the respective dental arch which faces the other dental arch. In particular, device 40 is an upper-mounted device that is essentially a unitary body 42 having an inner surface 44 secured to the lingual surface of upper incisors U and an outer surface 46 including a contact area 48 that generally faces lower incisors L. Device 40 as shown includes detents 49, a preferred feature that aids in securing device 40 to upper incisors U with a suitable adhesive, cement, or bonding agent, for example. Analogously, device 50 is a lower-mounted device that is essentially a unitary body 52 having an inner surface 54 secured to the labial surface of lower incisors L and an outer surface 56 including a contact area 58 that generally faces upper incisors U. Device 50 is shown as including detents 59. It will be noted that lower mounted device 50, unlike upper mounted device 40, extends over the incisal edge of the incisor to which it is mounted. This is because, for a normal jaw, the point of contact of jaw closure on the lower incisor is typically closer to the incisal edge than the point of contact on the upper incisor, which is typically toward the bottom of the lingual surface. Devices 40 and 50 may be retained on the respective tooth surface by cementation, bonding, or adhering, for example. Preferably, devices 40 and 50 are mounted to be removable by the user, but nonetheless securely enough to remain in place in the user's mouth through the user's nightly sleep, which is typically the time at which devices according to the present invention are most needed and most conveniently worn.

The foregoing descriptions of specific embodiments of the present invention are presented for purposes of illustration and description. They are not intended to be exhaustive or to limit the invention to the precise forms disclosed. Obviously, many modifications and variations are possible in view of the above teachings. While the embodiments were chosen and described in order to best explain the principles of the invention and its practical applications, thereby enabling others skilled in the art to best utilize the invention, various embodiments with various modifications as are suited to the particular use are also possible. The scope of the invention is to be defined only by the claims appended hereto, and by their equivalents.

What is claimed is:

1. An intra-oral device custom fit for a user, comprising:
a body having an angled front wall and an angled rear wall which meet to form an apex, the front wall having an inner and outer surface and the rear wall having an inner and outer surface, an outer surface of the body comprising the outer surfaces of the front and rear walls and an outer surface of the apex;
wherein the apex is configured to receive the incisal edges of the user's lower incisors;
wherein a portion of the outer surface of the body is configured to be disposed within the user's freeway space and not in contact with the user's upper teeth when the user is in the physiologic rest position and to prevent contact of the user's upper and lower premolars and molars when the user's mandible closes past the physiologic rest position.

2. The device according to claim 1, wherein the portion of the outer surface of the body is configured to be located within the user's freeway space to contact at least one of the user's upper incisors at an area of contact only within the freeway space.

3. The device according to claim 1, wherein the device is configured to allow the user's mandible to move along the mandibular hinge arc of closure until at least one of the user's upper incisors contacts the device.

4. The device according to claim 1,
wherein the inner surface of the front wall is configured to be placed adjacent to the labial surface of the user's lower incisors; and
wherein the inner surface of the rear wall is configured to be placed adjacent to the lingual surface of the user's lower incisors.

5. The device of claim 4,
wherein the inner surface of the front wall is configured to be placed substantially flush against the labial surface of the user's lower incisors; and
wherein the inner surface of the rear wall is configured to be placed substantially flush against the lingual surface of the user's lower incisors.

6. The device according to claim 4, further comprising an amount of moldable thermoplastic resin material disposed along the inner surfaces of the front and rear walls.

7. The device according to claim 6, further comprising means to retain the moldable material within the inner surfaces of the front and rear walls.

8. The device according to claim 7, wherein the means for retaining the moldable material comprise detents on the inner surfaces of the front and rear walls.

9. The device according to claim 7, wherein the means for retaining the moldable material comprise adhesive on the inner surfaces of the front and rear walls.

10. The device according to claim 6, wherein the thermoplastic resin material is capable of being molded at temperatures ranging from about 120 to about 180 degrees Fahrenheit.

11. The device according to claim 6, wherein the thermoplastic resin material is comprised of a resin selected from the group consisting of an ethylene vinyl acetate resin and a polycaprolactone resin.

12. The device of claim 6,
wherein the moldable thermoplastic resin material is capable of being molded by the user.

13. The device of claim 12,
wherein the inner surface of the front wall is configured to be placed adjacent to the labial surface of the user's lower incisors; and
wherein the inner surface of the rear wall is configured to be placed adjacent to the lingual surface of the user's lower incisors.

14. The device of claim 12,
wherein the device is configured to contact at least one upper incisor at an area of contact only within the user's freeway space.

15. A method for preventing head, neck, facial, joint and tooth pain, the method comprising:
placing a custom fit device within a user's oral cavity, the device having an angled front wall and an angled rear wall, each wall with an inner and outer surface, wherein the angles of the front wall and the rear wall form an apex with moldable thermoplastic resin material disposed along the inner surfaces of the front and rear wall, the apex configured to receive the incisal edges of the user's lower incisors; and
positioning the device such that the front wall of the device is adjacent to the labial surface of the user's lower incisors and the inner surface of the rear wall is disposed adjacent to the lingual surface of the lower incisors and the device does not contact the user's upper teeth when the user is in the physiologic rest position; and
placing the device to prevent contact of the user's upper and lower premolars and molars when the user's mandible is closed past the physiologic rest position.

16. The method according to claim 15, further comprising the step of molding the moldable thermoplastic resin material.

17. The method according to claim 15 further comprising the step of heating the moldable thermoplastic resin material to a molding temperature between about 120 and about 180 degrees Fahrenheit.

18. The method according to claim 15 wherein the combined thickness of the device's front wall and the moldable thermoplastic resin material prior to molding is approximately 1.5 millimeters.

19. The method according to claim 15 wherein the device preventing contact between the user's posterior teeth comprises the device contacting at least one of the user's upper incisors at an area of contact only within the user's freeway space.

20. The method according to claim 19 wherein contact on the device by at least one of the user's upper incisors causes the user's jaw muscles to reflexively relax to withdraw from contact on the upper incisors and open the user's mandible to the physiologic rest position.

21. A method for manufacturing an intra-oral device to be custom fit for a user, the method comprising:
forming a shell having an angled front wall and an angled rear wall, each wall with an inner and outer surface, wherein the angles of the front wall and the rear wall are configured to receive the incisal edges of the user's lower incisors;
configuring the inner surface of the front wall of the device to fit against the labial surface of the user's lower incisors;
configuring the inner surface of the rear wall to fit against the lingual surface of the user's lower incisors within the user's freeway space;
configuring the device not to contact the user's upper teeth when the user's mandible is in the physiologic rest position; and
adhering to the inner surfaces of the front and rear walls a moldable thermoplastic resin material.

22. The method of claim 21, wherein the shell is formed from plastic.

23. The method of claim 21, wherein the moldable thermoplastic resin material is capable of being molded at a temperature range from about 120 to about 180 degrees Fahrenheit.

24. The method of claim 21, further comprising configuring the inner surface of the front wall to fit substantially flush against the labial surface of the user's lower incisors and the inner surface of the real wall to fit substantially flush against the lingual surface of the user's lower incisors.

25. An intra-oral device custom fit for a user, comprising:
a body having an angled front wall and an angled rear wall which meet to form an apex, the front wall having an inner and outer surface and the rear wall having an inner and outer surface;
wherein the apex is configured to receive the incisal edges of a user's lower incisors;
wherein a portion of the outer surface is configured to fit within the user's freeway space to permit the incisal edge of the user's upper incisors to be located lower than the incisal edge of the user's lower incisors without the user's upper incisors contacting the device; and
wherein the device is configured to prevent contact of the user's upper and lower premolars and molars when the user's mandible closes past the physiologic rest position.

26. The device of claim 25, wherein the front wall is configured to fit substantially flush against the labial surface of the user's lower incisors.

27. An intra-oral device custom fit for a user comprising:
a body having an outer surface and an inner surface, the inner surface configured to be secured to at least one of the incisors of one of a user's dental arches, the outer surface including an area of contact generally facing the other dental arch, the area of contact defining a point along the arc of closure of the user's mandible at which at least one incisor of the other dental arch contacts the device when the user's mandible closes past the physiologic rest position;
wherein the area of contact is configured to be disposed within the user's freeway space and not in contact with the teeth of the other dental arch when the user is in the physiologic rest position and to prevent contact of the user's upper and lower premolars and molars when the user's mandible closes past the physiologic rest position.

28. The device of claim 27, wherein the body is rigid.

29. The device of claim 27, wherein the body is of unitary construction.

30. The device of claim 27, the inner surface of the body being configured to be secured to the lingual surface of at least one of the user's upper incisors, without covering any part of the labial surface of any of the user's upper incisors.

31. The device of claim 27, the inner surface of the body being configured to be secured to the labial surface of at least one of the user's lower incisors by a material selected from the group consisting of an adhesive, a cement, or a bonding agent.

* * * * *